(12) United States Patent
Myers

(10) Patent No.: US 6,168,653 B1
(45) Date of Patent: Jan. 2, 2001

(54) PRESSURE TRANSMISSION APPARATUS

(75) Inventor: Jan Willem Marinus Myers, Venlo (NL)

(73) Assignee: Filtertek, Inc

( * ) Notice: Under 35 U.S.C. 154(b), the term of this patent shall be extended for 0 days.

(21) Appl. No.: 09/079,978

(22) Filed: May 15, 1998

(30) Foreign Application Priority Data

May 15, 1997 (DE) ............................................. 297 08 673

(51) Int. Cl.⁷ .................................................. B01D 63/00
(52) U.S. Cl. .................................. 96/4; 55/495; 55/503; 55/511
(58) Field of Search ............................. 55/491, 495, 497, 55/503, 502, 510, 511; 95/45; 96/4

(56) References Cited

U.S. PATENT DOCUMENTS

| | | | |
|---|---|---|---|
| 3,238,056 | * 3/1966 | Pall et al. ................................ | 117/98 |
| 3,782,083 | * 1/1974 | Rosenberg .............................. | 55/491 |
| 3,932,153 | * 1/1976 | Byrns ...................................... | 55/511 |
| 3,966,520 | 6/1976 | Fallenbeck et al. . | |
| 4,148,732 | * 4/1979 | Burrow et al. .......................... | 55/503 |
| 4,404,006 | * 9/1983 | Williams et al. ....................... | 55/497 |
| 4,459,139 | 7/1984 | vonReis et al. . | |
| 4,670,510 | * 6/1987 | Kobayashi et al. .................... | 525/89 |
| 4,874,513 | * 10/1989 | Chakraborty et al. ................. | 55/503 |
| 4,986,904 | * 1/1991 | Buger et al. ............................ | 55/510 |
| 5,011,555 | * 4/1991 | Sager ...................................... | 55/491 |
| 5,147,545 | * 9/1992 | Despard et al. ........................ | 55/510 |
| 5,230,727 | * 7/1993 | Pound et al. ........................... | 55/511 |
| 5,269,917 | * 12/1993 | Stankowski ............................ | 55/511 |
| 5,443,723 | * 8/1995 | Stankowski et al. .................. | 55/511 |
| 5,500,003 | 3/1996 | Guala et al. ........................... | 604/252 |
| 5,603,792 | 2/1997 | Guala et al. ........................... | 156/245 |
| 5,749,861 | 5/1998 | Guala et al. ........................... | 604/249 |
| 6,086,762 | * 7/2000 | Guala .................................... | 210/232 |

FOREIGN PATENT DOCUMENTS

| | | |
|---|---|---|
| 2502673 A1 | 7/1976 | (DE) . |
| 29501239.0 | 4/1995 | (DE) . |
| 0 887 085 A2 | 12/1998 | (EP) . |
| 811818 | 4/1959 | (GB) . |

OTHER PUBLICATIONS

Christians, Rolf. (Apr. 1980) "Membranen in der Pneumatik", *Fluid.* pp. 39–46.

* cited by examiner

*Primary Examiner*—Duane S. Smith
(74) *Attorney, Agent, or Firm*—Brinks Hofer Gilson & Lione

(57) ABSTRACT

An apparatus for the transmission of the pressure in the sterile area of a medical appliance to a non-sterile pressure gauge has two housing halves and a sterility filter positioned between the two housing halves. The filter is supported by a backing. The housing half on the sterile side is made of polycarbonate. The non-sterile half of the housing is made of a polymer, preferably a polyester/polyether copolymer, which provides an easily disconnectable and leak-proof connection with the pressure gauge. The two halves are ultrasonically welded together.

18 Claims, 3 Drawing Sheets

Detail A

Detail B

PRESSURE TRANSMISSION APPARATUS

BACKGROUND OF THE INVENTION

The present invention relates to an apparatus for the transmission of the pressure in the sterile area of a medical appliance to a non-sterile pressure gauge. Pressure transmission apparatus of this kind, for example, are used in hemo-dialyzers, heart-lung-machines and similar medical appliances, in which a very accurate monitoring of the existing pressures in a sterile hose system is necessary, wherein simultaneously a sterilizing of the corresponding pressure gauges is not possible.

Such pressure transmission apparatus has to be absolutely sealed and free of leakage to prevent the non-sterile air from gaining access into the sterile area of the medical appliances, or to prevent mistakes in the measuring of the pressure. Further, such pressure transmission apparatus should have a so-called "Luer-Lock"-connector on the non-sterile side, preferably consisting of a polyester/polyether-copolymer to provide an easily disconnectable but simultaneously absolutely leak-proof connection with the corresponding stainless steel connectors of the pressure gauges in the medical appliance.

Prior art pressure transmission apparatus of this kind was constructed such that the housing consisted of a sterile half of polycarbonate having a hose connector and a non-sterile half, wherein between these two halves there was positioned a backing of polytetrafluorethylene carrying a polyfluorethylene sheet for the pressure transmission while simultaneously assuring the absolute impermeability. The corresponding "Luer-Lock"-connector on the non-sterile side had to be injection molded in a separate injection molding apparatus when producing the non-sterile side half of the housing. The expert in the art was of the opinion that this kind of production cannot be avoided because the expert had the prejudice that an absolutely sealed and leak-free connection between a part consisting of polyester-polyether-copolymer and a part consisting of polycarbonate was only possible by the cumbersome co-injection molding method, and was not possible by ultrasonic welding. Further, a completely sealed fixing of the backing carrying the polytetrafluorethylene sheet was only believed to be possible between two housing halves consisting of polycarbonate because of the fact that the polyester/polyether-copolymer was too soft for this purpose.

SUMMARY OF THE INVENTION

Starting out from this prior art, one aim of the present invention is to provide a pressure transmission apparatus of the above-identified kind which has the same quality (impermeability and leak-proof) but can be produced in a drastically more simple and cheaper manner.

According to the invention, this aim is achieved by the fact that the non-sterile half of the housing consists of polyester/polyether-copolymer and that the two halves are connected by ultrasonic welding.

Contrary to the prejudice in the related expert field, the present invention is based on the finding that a sufficiently impermeable and leak-proof ultrasonic welding between one housing half of polyester/polyether-copolymer and another housing half of polycarbonate can be produced.

In this connection, it is of special advantage that the backing carrying the polytetrafluorethylene sheet is produced from polyester. This has the substantial advantage that the backing is also welded during the ultrasonic welding of the two housing halves, which leads to a substantially improved fixing and sealing of the backing.

Further, it is preferred that the non-sterile half of the housing has a thin circumferential projection which partly overlies the sterile half of the housing and which forms an ultrasonic welding area. By this, the ultrasonic welding is made not only possible but extremely simple, safe and cheap.

Further, it is especially preferred that within the projection a circumferential groove is provided in the non-sterile half into which a projection of the sterile half meshes. By this, the ultrasonic welding area is enlarged and the impermeability and strength of the connection between the two housing halves is further improved.

It is especially preferred in this connection that the projection on the sterile half has on its exterior a bevel in the direction of the non-sterile half. By this, a narrow, wedge-shaped, circumferential cavity is formed on the non-sterile end of the welding area into which the material softened during the ultrasonic welding can move, whereby the quality of the weld is further improved.

Further, it is especially preferred to provide a bevel on the inner side of the groove. By this, the mounting of the two housing halves is simplified and additional room is created into which the material softened by the ultrasonic welding can move.

The invention is described in more detail with reference to the attached drawings.

DETAILED DESCRIPTION OF THE DRAWINGS AND PREFERRED EMBODIMENT

Figure 1:
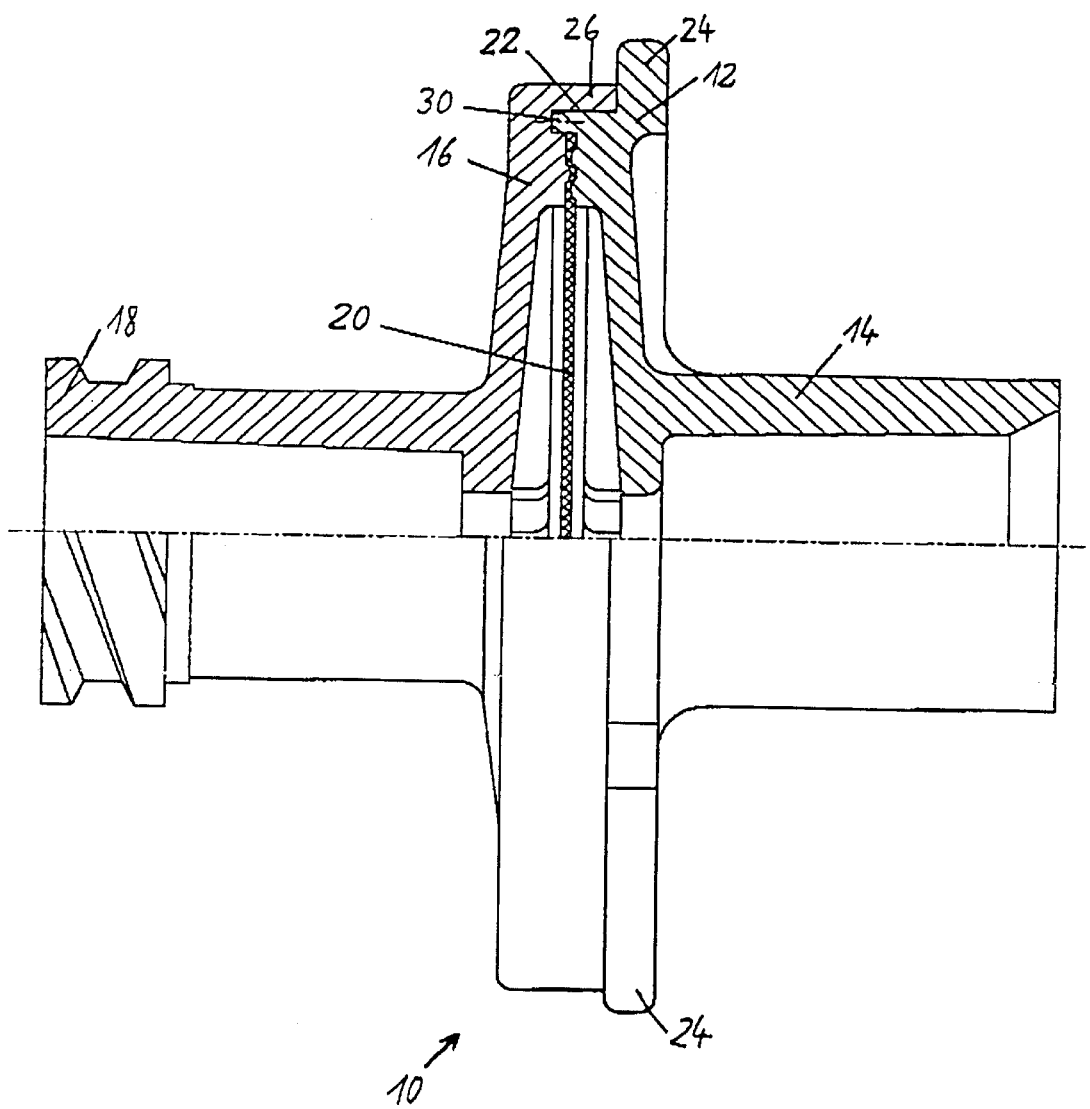
FIG. 1 is a complete pressure transmission apparatus according to the invention, partly in section.

As shown in FIG. 1, the housing 10 of a preferred pressure transmission apparatus according to the invention comprises a sterile housing half 12, including a hose connector 14, consisting of polycarbonate, and a non-sterile housing half 16 having a "Luer-Lock" connector 18, which, according to the preferred embodiment of the invention, is made of polyester/polyether-copolymer. Between the two housing halves 12 and 16, a backing 20 of polyester is held under pressure and is welded in its place during the ultrasonic welding of the two housing halves 12 and 16. The backing 20 carries a thin sheet of polytetrafluorethylene which performs the filter function between the sterile and the non-sterile areas. The polytetrafluorethylene sheet has such a small pore size that air can pass through but any non-sterile items in the air are blocked. Thus pressure changes in the sterile side can be transmitted to the non-sterile side, where a gauge or other pressure sensitive device is connected The ultrasonic welding of the two housing halves 12 and 16 occurs in the area designated with reference number 22.

Figure 2:
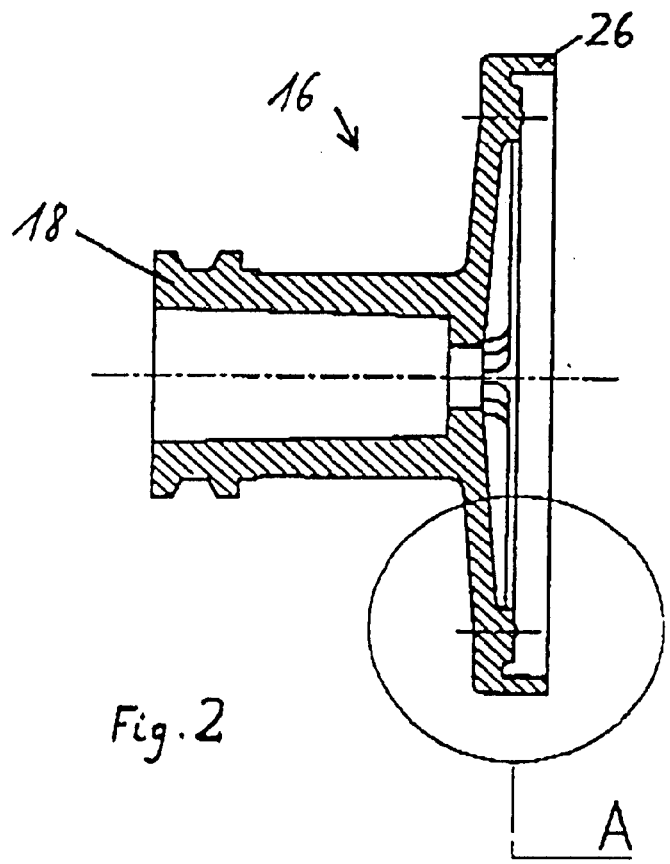
FIG. 2 a cross-sectional view of the non-sterile housing half of the pressure transmission apparatus according to the invention shown in FIG. 1.
Figure 3:
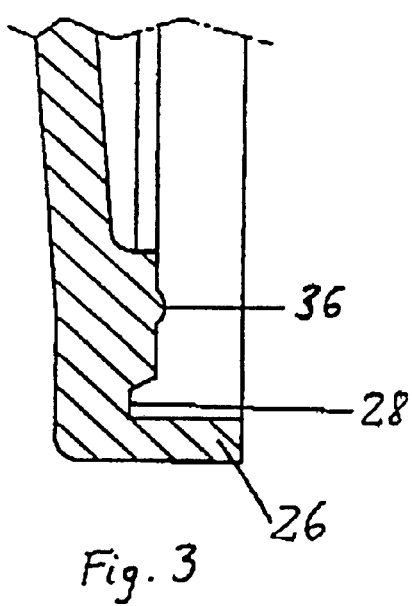
FIG. 3 an enlarged view of the detail A of FIG. 2.
Figure 4:
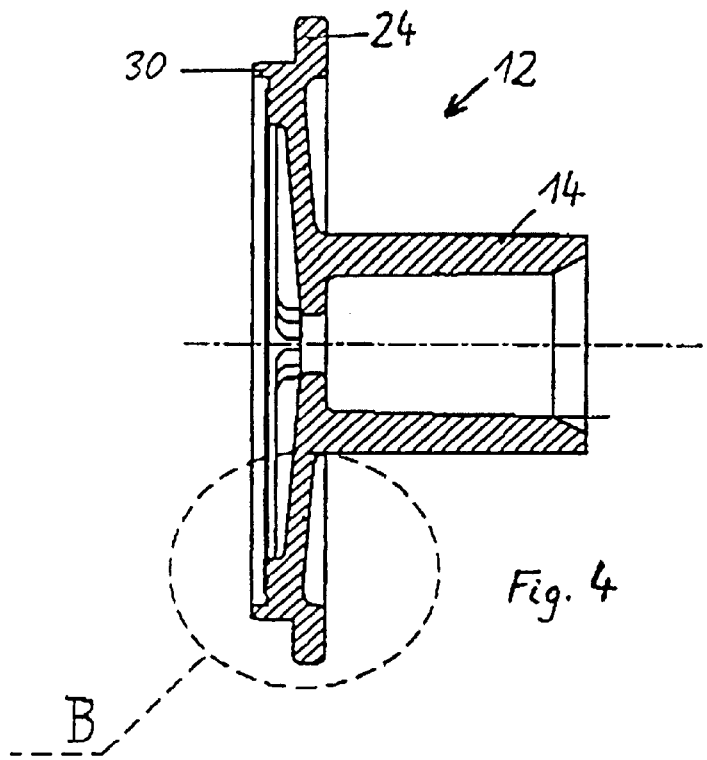
FIG. 4 a cross-sectional view of the sterile housing half of the pressure transmission apparatus according to the invention shown in FIG. 1 and, FIG. 5 an enlarged view of the detail B of FIG. 4.
Figure 5:
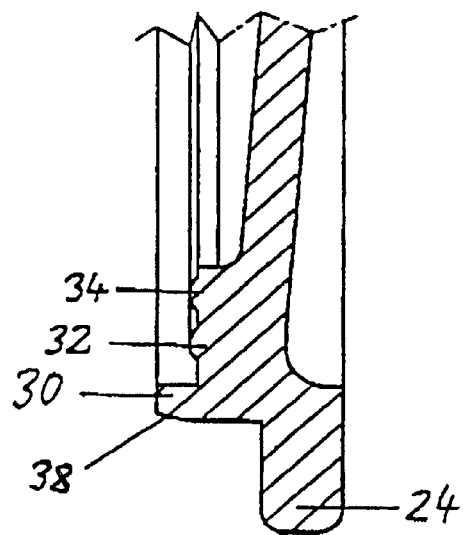

The two housing halves 12 and 16 each have a shape such that the entire construction has a rotational symmetry. The connection between the two housing halves 12 and 16 in detail is obtained as follows:

The sterile housing half 12 (FIGS. 4 and 5) has an exterior outer circumferential ring 24. This ring 24 serves as an abutment for a thin circumferential projection 26 (FIGS. 2 and 3) extending from the non-sterile housing half 16 in the direction of the sterile housing half 12. A circumferential groove 28 is provided in the non-sterile housing half 16 within the projection 26. A projection 30 of the sterile housing half 12 meshes into this groove 28. This projection 30 is provided with a bevel 38 on its exterior on the end facing the non-sterile housing half 16 such that the thickness of the projection 30 is decreasing in the direction of the non-sterile housing half 16.

The ultrasonic welding connection occurs in the area 22 from the exterior thereof and in a circumferential direction. The bevel 38 creates a cavity in the groove 28 into which the material molten by the ultrasonic welding can move. On the inner side of the groove 28 in the non-sterile housing half 16 another bevel is provided also, to ensure an easy mounting and additionally to create a further space into which the material molten during the ultrasonic welding can move.

Within the projection 30 or the groove 28, respectively, the backing 20 is held under pressure between the two housing halves 12 and 16, wherein the backing 20 carries the polytetrafluorethylene sheet for sealing the sterile area from the non-sterile area. The backing 20 preferably consists of polyester. Two concentric rings 32 and 34 which project slightly are provided on the sterile housing half 12 (FIG. 5) to improve the fixation and sealing of the backing 20 between the two housing halves 12 and 16. A single circumferential ring 36 (FIG. 3) projects from the non-sterile housing half 16 from an area opposed to the area between these two rings 32 and 34.

For mounting the pressure transmission apparatus, a backing 20 having the polytetrafluorethylene sheet is positioned in a sterile housing half, the non-sterile housing half is plugged in and the two housing halves are sealingly connected with each other by circumferential ultrasonic welding. By this method of production, the pressure transmission apparatus can be produced much cheaper compared with the prior art.

It should be appreciated that the apparatus of the present invention is capable of being incorporated in the form of a variety of embodiments, only one of which has been illustrated and described above. The invention may be embodied in other forms without departing from its spirit or essential characteristics. The described embodiment is to be considered in all respects only as illustrative and not restrictive, and the scope of the invention is, therefore, indicated by the appended claims rather than by the foregoing description. All changes which come within the meaning and range of equivalency of the claims are to be embraced within their scope.

I claim:

1. An apparatus for the transmission of the pressure in the sterile area of a medical appliance to a non-sterile pressure gauge having a non-sterile connector of polyster/polyether-copolymer and a connector on the sterile side consisting of polycarbonate, wherein between the two connectors there is provided a sterility filter consisting of polytetrafluorethylene, which is positioned in a fluid-tight manner between two halves of the housing, said filter being supported by a backing, wherein the housing half on the sterile side comprises polycarbonate, characterized in that the non-sterile half of the housing consists of polyester/polyether-copolymer and in that the polycarbonate of the housing half on the sterile side is connected to the polyester/polyether-copolymer of the other housing half by ultrasonic welding.

2. The apparatus according to claim 1, characterized in that the backing comprises polyester.

3. The apparatus according to claim 1, characterized in that the non-sterile half of the housing has a thin circumferential projection which partly overlies the sterile half of the housing thereby forming an area for ultrasonic welding.

4. The apparatus according to claim 3, characterized in that a circumferential groove is provided in the projection in the non-sterile half into which a projection of the sterile half engages.

5. The apparatus according to claim 4, characterized in that the projection of the sterile half is provided with a bevel in the direction of the non-sterile half.

6. The apparatus according to claim 4, characterized in that the groove is bevelled on its inner side.

7. A pressure transmission apparatus comprising:

a) a first housing half comprising polyester/polyether copolymer;

b) a second housing half comprising polycarbonate;

c) a sterility filter supported by a backing disposed between the first and second housing halves in a fluid tight manner; and d) the first and second housing halves being connected by ultrasonically welding together the polyester/polyether copolymer and the polycarbonate.

8. The apparatus of claim 7 wherein the backing comprises polyester.

9. The apparatus of claim 8 wherein the polyester backing is welded to the polyester/polyether copolymer housing.

10. An apparatus for the transmission of pressure in the sterile area of a medical appliance to a non-sterile pressure gauge comprising a sterility filter consisting of polytetrafluorethylene, which is positioned in a fluid-tight manner between two halves of a housing, said filter being supported by a backing, wherein the housing half on the sterile side comprises polycarbonate, and the non-sterile half of the housing comprises a second polymer different than polycarbonate and able to provide an easily disconnectable and leak-proof connection with the pressure gauge, the two halves being connected by ultrasonic welding the polycarbonate to the second polymer.

11. The apparatus of claim 10 wherein the second polymer comprising the non-sterile housing half is a copolymer.

12. The apparatus of claim 11 wherein the copolymer is a polyester/polyether copolymer.

13. A pressure transmission apparatus comprising:

a) a first housing half comprising polyester;

b) a second housing half comprising polycarbonate;

c) a sterility filter supported by a backing disposed between the first and second housing halves in a fluid tight manner; and d) the first and second housing halves being connected by ultrasonically welding together the polyester and polycarbonate.

14. The pressure transmission apparatus of claim 13 wherein the polyester is part of a copolymer.

15. A pressure transmission apparatus comprising:

a) a first housing half comprising a soft polymer;

b) a second housing half comprising polycarbonate;

c) a sterility filter of polytetrafluorethylene supported by a backing made of polyester disposed between the first and second housing halves in a fluid tight manner; and d) the first and second housing halves being connected by ultrasonically welding together the soft polymer and the polycarbonate.

16. The pressure transmission apparatus of claim 15 wherein the soft polymer comprises a polyester.

17. The pressure transmission apparatus of claim 16 wherein the polyester is part of a copolymer.

18. The pressure transmission apparatus of claim 16 wherein the polymer comprises a polyester/polyether copolymer.

* * * * *

UNITED STATES PATENT AND TRADEMARK OFFICE
CERTIFICATE OF CORRECTION

PATENT NO. : 6,168,653 B1  
DATED : January 2, 2001  
INVENTOR(S) : Jan W. Marinus Myers It is certified that error appears in the above-identified patent and that said Letters Patent is hereby corrected as shown below:

<u>Title page,</u>  
Under "U.S. PATENT DOCUMENTS" line 10, delete "Buger" and substitute -- Bugar -- in its place.

<u>Claim 1,</u>  
Line 3, delete "polyster" and substitute -- polyester -- in its place.

Signed and Sealed this

Ninth Day of April, 2002

Attest:

Attesting Officer

JAMES E. ROGAN  
Director of the United States Patent and Trademark Office